US005834200A

United States Patent [19]
Rousseau

[11] Patent Number: 5,834,200
[45] Date of Patent: Nov. 10, 1998

[54] MARKER AT THE ESTROGEN RECEPTOR GENE FOR DETERMINATION OF OSTEOPOROSIS PREDISPOSITION

[75] Inventor: François Rousseau, Ste-Foy, Canada

[73] Assignee: Universite Laval, Cite Universitaire, Quebec, Canada

[21] Appl. No.: 892,248

[22] Filed: Jul. 14, 1997

Related U.S. Application Data

[63] Continuation of Ser. No. 592,835, Jan. 25, 1996, abandoned.

[51] Int. Cl.⁶ .............................. C12Q 1/68; C12P 19/34; C07H 21/04
[52] U.S. Cl. ........................... 435/6; 435/91.2; 536/24.3; 536/24.31; 935/77; 935/78
[58] Field of Search ..................... 435/6, 91.2; 536/24.3, 536/24.31; 935/77, 78

[56] References Cited

U.S. PATENT DOCUMENTS

| | | | |
|---|---|---|---|
| 5,374,526 | 12/1994 | Rothschild et al. | 435/6 |
| 5,550,024 | 8/1996 | Rothschild et al. | 435/6 |
| 5,593,833 | 1/1997 | Morrison et al. | 435/6 |

FOREIGN PATENT DOCUMENTS

| | | |
|---|---|---|
| 08214899 | 8/1996 | Japan . |
| WO 88/08457 | 11/1988 | WIPO . |
| WO 94/03633 | 2/1994 | WIPO . |
| WO 96/22387 | 7/1996 | WIPO . |

OTHER PUBLICATIONS

Crow, J.F., "Basic Concepts in Population, Quantitiative, and Evolutionary Genetics", New York: W.H. Freeman, 1986, pp. 19–23.

del Senno et al., Human Molecular Genetics, 1992 1:354.

Morrison et al., Nature, 1994 367:284–287.

Sano et al., Biochem. Biophys. Res. Comm. 1995, 217:378–383.

Yaich et al., Cancer Research, 1992, 52:77–83.

Fleet et al. The Bsml Vitamin D Receptor Restriction Fragment Length Polymorphism (BB) Predicts Low Bone Density in Premenopausal Black and White Women. Journal of Bone and Mineral Research 10(6):985–990, 1995.

Yaich et al. Analysis of the PvuII Restriction Fragment–Length Polymorphism and Exon Structure of the Estrogen Gene in Breast Cancer and Peripheral Blood. Cancer Research 52:77–83, 1992.

Riggs et al. Involutional Osteoporosis. The New England Journal of Medicine 314(6):1676–1684, 1986.

Kobayashi et al. Association of Bone Mineral Density with Polymorphism of the Estrogen Receptor Gene. Journal of Bone and Mineral Research 11(3):306–311, 1996.

*Primary Examiner*—George C. Elliott
*Assistant Examiner*—Thomas G. Larson
*Attorney, Agent, or Firm*—Clark & Elbing LLP

[57] ABSTRACT

The present invention relates to a method of determining predisposition to low or high bone mineral density and to development of osteoporosis of a patient, which comprises determining estrogen receptor polymorphism in linkage disequilibrium in a biological sample of said patient, wherein heterozygosity is associated with high bone density and homozygosity is associated with low bone density.

12 Claims, 1 Drawing Sheet

MARKER AT THE ESTROGEN RECEPTOR GENE FOR DETERMINATION OF OSTEOPOROSIS PREDISPOSITION

This is a continuation of application Ser. No. 08/592,835, filed Jan. 25, 1996, now abandoned.

BACKGROUND OF THE INVENTION (a) Field of the Invention

The invention relates to a method of determining genetic predisposition to low or high bone mineral density of a patient, wherein low bone density is indicative of a predisposition to osteoporosis and high bone density is indicative of resistance to osteoporosis.

(b) Description of Prior Art

Osteoporosis, a reduction of bone mineral density (BMD), is a multifactorial disease that leads to an increasing risk of fracture and is becoming a major public health problem, especially in post-menopausal women. Its major consequence, hip fracture, has major health consequences with serious social, medical and economical implications in increasingly aging populations. Research on osteoporosis emphasizes at either finding new therapeutic approaches or at the characterization of the major determinants of bone mineral density (BMD) in the hope to find markers useful in identification of women at risk of osteoporosis and its complications. Since therapy of established osteoporosis remains far from satisfactory, prevention is the best choice.

Heredity has always been considered an important risk factor for osteoporosis, but its role was still poorly understood, at least until recently. Indeed, several studies of monozygotic (MZ) and dizygotic (DZ) twins have shown that BMD was better correlated between MZ than DZ twins, indicating that BMD is genetically determined and that heredity could account for up to 80 to 90% of the variability in BMD. Intra and intergeneration correlations were more contradictory, two studies showing significantly lower BMD in daughters of women with osteoporosis while another mother/daughter pairs study found no such difference. Since a decrease of one standard deviation in BMD within normal range approximately doubles the risk of fracture at different skeletal sites, the search for a marker likely to identify women at risk of post-menopausal osteoporotic fractures is becoming more and more relevant.

More recently, a group of investigators have highlighted that polymorphism in the vitamin D receptor (VDR) gene were significantly correlated with the levels of osteocalcin, a marker of bone turnover. The same Australian group studied a cohort of 250 healthy twins for BMD and a polymorphism at the VDR revealed by the restriction enzyme Bsm I and found that genotype at the VDR could explain up to 75% of the genetic variation in BMD at the lumbar vertebrae and proximal femur. The BB genotype, where B represents the allele with absence of the restriction site and b represents the allele with the polymorphic Bsm I site, is associated with lower BMD and likely to an increased predisposition to osteoporosis. The bb genotype was associated to a higher BMD and the Bb genotype was associated with intermediate BMD. Moreover, they studied 311 unrelated healthy women and confirmed that genotype at the VDR locus was a strong predictor of BMD at both lumbar and femoral sites. The authors used an in vitro model (minigene model) suggesting that the VDR gene allelic variation could influence the rate of the receptor protein synthesis (Morrisson NA et al., *Nature*, 1994, 367:284–297).

Many other groups have now published their results on different populations which are contradictory. A twin study done in the United Kingdom confirmed the association between VDR genotype and BMD adjusted for body mass index (BMI). Another twin study in Indiana showed that up to 70% of the BMD could be attributed to heredity but did not find any relationship between VDR polymorphism and BMD. Another study concentrated on mother/daughter pairs in a Swiss population and found that VDR alleles contributed to mother/daughter BMD relationship. This study also showed that VDR polymorphism was associated with femoral BMD in teenage girls and pre-menopausal women. Another group from Massachusetts showed that the BB genotype was associated with significantly lower BMD compared to Bb and bb genotypes in both black and white races in a cohort of healthy unrelated pre-menopausal women aged 20 to 40. This suggested that the VDR polymorphism may limit peak bone mass.

Two studies from Japan on healthy unrelated women concluded that there was a difference in allele frequencies between Caucasian and Asian populations. One group found an association between VDR genotype and BMD at the lumbar vertebrae but the trend was more apparent in pre than post-menopausal women. The other Japanese group concentrated on post-menopausal women and confirmed the association between VDR polymorphism and lumbar BMD but the genotype could not predict total BMD and had little clinical significance in the evaluation of bone status in Japanese women. Recently, a group from the Netherlands found an association between VDR alleles and BMD, but the allele previously described as "protective" against osteoporosis was associated with lower BMD at the femoral neck and Ward's triangle, suggesting allelic heterogeneity at the VDR locus.

Two studies looked at allelic frequencies in both normal and osteoporotic women. One group from Sweden found a 2.2 fold increase in the prevalence of the predisposing BB genotype in severely osteoporotic women compared to normal healthy controls but the relationship did not seem to reach statistical significance. The other group from Minnesota, did not find a significant difference in genotype prevalence. They also noted that the effect of VDR genotype on BMD was modulated by age, with a greater effect in pre-menopausal women, reinforcing the hypothesis that allelic variations at the VDR locus may influence peak bone mass.

Finally, a longitudinal study was recently published where lumbar and proximal femoral BMD were measured every six months for eighteen months in a cohort of elderly Swiss men and women. They concluded that the rate of bone loss was associated to VDR genotype at the lumbar spine but not at the femoral neck. BB genotype showed greater rate of bone loss, irrespective of calcium intake or supplement, but the rate of bone change for Bb genotype was influenced by overall calcium intake.

The International Patent application No. WO 94/03633 (published on Feb. 17, 1994) discloses a genetic test for assaying a predisposition to and/or resistance to high rates of bone turnover, development of low bone mass and responsiveness to therapeutic treatment. This test can be used for predicting osteoporosis and likely response to preventive or therapeutic modalities. The test essentially consists in assessing the allelic variations in the vitamin D receptor gene.

SUMMARY OF THE INVENTION

One aim of the present invention is to provide a method of determining predisposition to low or high bone density of a patient, which comprises determining estrogen receptor polymorphism in a biological sample of the patient, wherein heterozygosity is associated with high bone density and homozygosity is associated with low bone density.

Another aim of the present invention is to provide means to screen women to identify those for which the more expensive formal measurement of BMD is indicated.

Another aim of the present invention is to provide means of identifying young women that will be at risk of osteoporosis after their menopause so that they can attempt to increase their BMD to reach a higher peak bone mass.

Another aim of the present invention is to provide means of identification of target sub-groups of women for osteoporosis prevention measures/programs.

Another aim of the present invention is to provide means to determine which sub-group of post menopausal women will most benefit from osteoporosis treatment(s) and eventually predict their response to therapy or choose the optimal preventive pharmacotherapy.

Another aim of the present invention is to identify means of prediction and management of BMD as well as biological parameters for the establishment of population-based osteoporosis prevention and intervention programs.

In accordance with the present invention there is provided a method of determining predisposition to low or high bone mineral density and to development of osteoporosis of a patient, which comprises determining estrogen receptor polymorphism in a biological sample of the patient, wherein heterozygosity is associated with high bone density and homozygosity is associated with low bone density.

In some embodiments, the method of the present invention includes detecting the estrogen receptor polymorphism by analyzing the restriction fragment length polymorphism using an endonuclease digestion. The method can further include a step prior to the estrogen receptor gene digestion, wherein at least a fragment of the estrogen receptor is amplified, for example, by polymerase chain reaction.

In accordance with the present invention, the estrogen receptor polymorphism, without limitation, is selected from the group consisting of PvuII polymorphic site located in the first intron of the ER gene or any DNA variant or mutation which shows some degree of linkage disequilibrium with one of the alleles of the PvuII polymorphism.

The polymorphism of the estrogen receptor gene can be detected using at least one oligonucleotide specific to the normal or variant estrogen receptor gene allele.

In accordance with the present invention, low bone density is indicative of a predisposition to osteoporosis and/or bone fracture of the patient post-menopause, while high bone density is indicative of a resistance to osteoporosis and/or bone fracture of the patient post-menopause.

In accordance with the present invention, estrogen receptor genotyping is indicative of response to therapy and/or to preventive treatments against low bone mineral density and bone and vertebrae fractures.

The present invention also provides a kit for determining predisposition to low or high bone mineral density of a patient, which includes at least a probe specific for the estrogen receptor;

an endonuclease selected from the group consisting of PvuII, PssI, SacI, and XbaI.

Also, in accordance with the present invention, there is provided a method of determining predisposition to estrogen hormone-related medical conditions of a patient, including the steps of:

a) isolating nucleic acid of the patient from a biological sample;

b) determining the genotype in said isolated nucleic acid of step a), wherein said genotype corresponds to a region including the gene encoding the estrogen receptor, and wherein heterozygosity or homozygosity is indicative of predisposition of said estrogen hormone-related medical conditions and homozygosity or heterozygosity is indicative of likelihood of protection against said estrogen hormone-related medical conditions.

For the purpose of the present invention the following abbreviations and terms are defined below.

The abbreviation "RFLP" refers to restriction fragment length polymorphism.

The term "DNA polymorphism" or "polymorphic DNA sequence" refers to any sequence in the human genome that exists in more than one variant (or version) in the population.

The term "estrogen hormone-related medical conditions" refers to, without limitation, any estrogen-dependent diseases such as osteoporosis, endometriosis, arteriosclerosis, breast cancer, ovarian cancer and other estrogen-dependent cancers, among others.

The term "linkage disequilibrium" refers to any degree of non-random genetic association between one or more allele (s) of two different polymorphic DNA sequences and that is due to the physical proximity of the two loci. Linkage disequilibrium is present when two DNA segments that are very close to each other on a given chromosome will tend to remain unseparated for several generations with the consequence that alleles of a DNA polymorphism (or marker) in one segment will show a non-random association with the alleles of a different DNA polymorphism (or marker) located in the other DNA segment nearby. Hence, testing of one of the DNA polymorphism (or marker) will give almost the same information as testing for the other one that is in linkage disequilibrium. This situation is encountered throughout all the human genome when two DNA polymorphisms that are very close to each other are studied. Such a linkage disequilibrium with several polymorphisms in the vitamin D receptor gene are reported in Morrisson et al., 1994. Various degrees of linkage disequilibrium can be encountered between two genetic markers so that some are more closely associated than others.

The terms "estrogen receptor polymorphism" or "genetic marker" are intended to include, without limitation, PvuII (GDB (Genome Data Base) #G00-155-446), PssI (GDB #G00- 155-447), SACI (GDB #G00-155-448), XbaI (GDB #G00-155-449) as well as the following ESR non-RFLP polymorphisms: GDB #G00- 162-450, #G00-162-541, and any other allelic variant of the estrogen receptor gene that shows some degree of linkage disequilibrium in any population sub-group with at least one of the above-mentioned estrogen receptor gene polymorphisms.

The estrogen receptor gene polymorphism site in accordance with the present invention can be located within the estrogen receptor gene or within 500 kb on each side of the ER gene, preferably within 250 kb, and more preferably within 50 kb.

DETAILED DESCRIPTION OF THE INVENTION

Figure 1A:
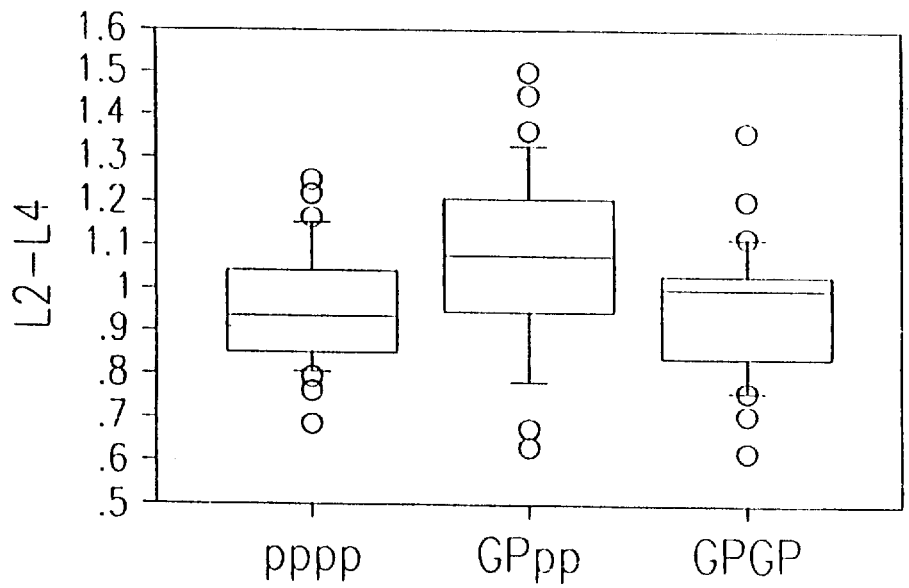
FIG. 1A is a box plot graph of the ER/PvuII RFLP genotyping results correlated with bone mineral density at the L2–L4 vertebraes.

The balance between bone formation and resorption is very complex and is a consequence of many factors (calcium and phosphor intake, PTH, estrogen's and androgens and 1,25-dihydroxy vitamin D amongst others). Accelerated bone resorption is seen in the first few years after menopause characterized by ovarian failure and estrogen deficiency. We hypothesized that allelic variation at the estrogen receptor (ER) gene could be related to BMD. A cohort of 88 healthy unrelated post-menopausal women aged between 60 and 70 were genotyped for a known PvuII DNA polymorphism in the first intron of the estrogen receptor (ER) gene (Yaich, *Cancer Res.*, 1992, 52:77–83). A strong relationship between the ER genotype status and BMD was found, the heterozygotes for this RFLP having a significantly higher BMD than the two homozygote groups. This suggests that heterodimer rather than homodimer ER formation of this trans-acting element would confer a selective advantage against osteoporosis either through its interaction with the ligand and/or with DNA where it acts as a transcription factor. Furthermore, genotyping of the same subjects for a dinucleotide repeat $(TA)_n$ 5' to the ER locus (del Senno L et al., *Hum. Mol. Genet.*, 1992, 1 (5):354) showed a strong bimodal allelic distribution and confirmed a decreased BMD in a subgroup of post-menopausal women but with less statistical power.

These findings may have important repercussions on the screening for low BMD in post-menopausal women but also for the implementation of screening programs aimed at preventing low BMD in women and for identification of women which would benefit from estrogen replacement therapy at their menopause. Also, it may be useful for other applications in the prevention and treatment of osteoporosis but perhaps on other important diseases or conditions showing an estrogen-dependent behavior (cancer, arteriosclerosis and endometriosis amongst others).

Subjects 88 healthy unrelated post-menopausal women aged between 60 and 70 were recruited. They were all Caucasian French-Canadian women from a French background and were all living in the Quebec city metropolitan area. Recruitment was achieved through voluntary response to local newspaper advertisements for a study on factors affecting BMD in healthy post-menopausal women, including genetic factors. The subjects had to answer a detailed questionnaire covering family, medical, surgical, genealogical and obstetrical history. The survey also included information about medications and life habits (exercise, tobacco, alcohol, etc.). All women between 60 to 70 who had accepted to sign consent form, answer adequately the questionnaire, have bone-mass measurement and a 30 mL blood puncture were included unless they had a medical condition affecting bone homeostasis, or had used medications that modify bone metabolism.

Bone density

BMD was measured at both the lumbar spine (L2–L4) and the femoral neck by dual-energy X-ray absorptimetry (DEXA, DPX-L Lunar Radiation Corporation, Madison, Wisc., USA, Software version 3.2). This technique is rapid, reliable and precise with a coefficient of variation of 1–2%.

DNA isolation

Blood samples were drawn into VACUTAINER containing EDTA and 200L was aliquoted in 1.5 mL EPPENDORF tubes within 48 hours and stored at −20° C. until DNA purification. Genomic DNA was isolated from peripheral blood leukocytes with a minimethod necessitating only 200 L of whole blood where all steps are processed in a single 1.5 mL tube as described below. Isolated DNA (5–7 g) was resuspended into 100 L TE 20:5 buffer (20 mM Tris, 5 mM EDTA), heated at 65° C. for 4 hours and stored at 4° C.

The whole procedure of DNA extraction takes place in a single 1.5 mL EPPENDORF tube, minimizing sample identification errors and sample mixing. All reagent concentrations and volumes added to the tube are set in order to use a pipette repeat dispenser all through the procedure. The number of samples processed in a single DNA extraction/digestion procedure depends only on the availability of places in centrifuges turning at 13000 RPM. BIOFUGE 15 (Heraus) benchtop centrifuges in a 4° C. room has a capacity of 80×1.5 mL EPPENDORF tubes. The tubes remain in the centrifuge's 10-tube holders all through the procedure which eliminates a lot of tube manipulation.

200 $\mu$L of whole blood (collected on EDTA) is placed in an appropriately identified 1.5 mL EPPENDORF tube. The same tube will be used until gel loading so it must be identified with a very resistant marking tool. A slightly heated metal tool may be used to engrave the number on the tube, this allows for permanent labeling.

1 mL of a 2 mM TRIS buffer+5 mM EDTA+0,5% NP-40 solution (TE20:5+NP40) is added to the samples and they are left on ice for 30 minutes to allow for membrane disruption. Then the tubes are centrifuged at 4000 RPM for 15 minutes and the supernatant is removed by gently shaking the tubes upside down over a sink. The pellets are then broken down by vortexing vigorously in a multitube vortex for a few minutes followed by two more washes with 1 mL TE20:5+NP40 and 15 min. at 4000 RPM followed by vortexing of the pellets at each time. Afterwards, the pellets are resuspended in 100$\mu$L TE20:5 (20 mM TRIS buffer+5 mM EDTA) and 10 $\mu$L of 10% sarcosine are added followed by 10 $\mu$L of 2 mg/mL Proteinase K (BMC). The samples are incubated at 37° C. overnight or 3 hours at 65° C.

After the proteinase K digestion is completed 100 $\mu$L ammonium acetate 7.5M are added and well mixed. Then 500 $\mu$L of pure ethanol (cooled at −20° C.) are added to each tube and mix well, allowing for DNA precipitation. There is enough DNA in each tube to actually see it precipitate when the cold ethanol is added.

The tubes are centrifuged for 10 min. at 13 000 RPM and the supernatant removed by gentle shaking over the sink. The pellet is then resuspended in 100 $\mu$L TE20:5 (without NP40) and reprecipitated with 100 $\mu$L ammonium acetate 7.5M and 500 $\mu$L of pure ethanol (cooled at −20° C.). Tubes are centrifuged for 10 min. at 13 000 RPM and the supernatant again discarded. The DNA pellet is dried under negative pressure for 10 min. (in a dessicator), then resuspended in 200 $\mu$L TE20:1 (20 mM TRIS buffer+1 mM EDTA) and left at 37° C. for a few hours to allow for dissolution of the final DNA pellet.

Pvu II polymorphism analysis

From the resuspended DNA, 200 ng of genomic DNA was amplified in a 100 $\mu$L volume containing 0.5 $\mu$M of both forward 5' TGCCACCCTATCTGTATCTTTTCC3' (SEQ ID No: 1) and reverse 5' TCTTTCTCTGCCACCCTG-GCGTC3' (SEQ ID No: 2) primers derived from Yaich (Yaich, *Cancer Res.*, 1992, 52:77–83), 200 $\mu$M of each of the four deoxyribonucleotides and 2.5 U of Taq polymerase and buffer (Promega) in 1.5 mM $MgCl_2$. PCR amplification included the following steps: initial denaturation for 7 min. at 96° C. followed by 35 cycles of amplification with denaturation at 94° C. for 60 s, annealing at 60° C. for 60 s and polymerase extension at 72° C. for 4 min. A final extension at 72° C. for 10 min. was also included.

About 500 ng of the PCR product were digested with 10 U Pvu II (New England Biolabs) overnight at 37° C. and the polymorphism was visualized by ethidium bromide staining after a 2% agarose gel electrophoresis. Absence of the site (P) resulted into a 1.3 Kb fragment whereas presence of the Pvu II site (p) resulted into 850 bp and 450 bp fragments which was consistent with published data (Yaich, *Cancer Res.*, 1992, 52:77–83).

TABLE 1

DNA extraction protocol for miniprep of genomic DNA
Place 200 μL of whole blood (collected on EDTA) in a 1.5 mL EPPENDORF tube;
Add 1 mL of TE20:5 + NP40 (20 mM TRIS buffer + 5 mM EDTA + 0, 5% NP-40), leave 30 min. on ice and centrifuge for 15 min. at 4 000 RPM;
Throw away the supernatant;
Perform one more wash with 1 mL TE20:5 + NP40, vortex and centrifuge for 15 min. at 4000 RPM;
Resuspend the pellet in 100 μL TE20:5 and vortex well;
Add 10 μL of 10% sarcosine and then 10 μL of Proteinase K (BMC) at 2.5 mg/mL and incubate at 37° C. overnight or 3 hours at 65° C.;
Add 100 μL Ammonium acetate 7.5M, mix well and then add 500 μL of pure ethanol (cooled at −20° C.), mix well and centrifuge for 10 min. at 13 000 RPM;
Remove the supernatant and resuspend the pellet in 100 μL TE20:5 (without NP40)
Reprecipitate with 100 μL Ammonium acetate 7.5M, mix well and 500 μL of pure ethanol (cooled at −20° C.), mix well and centrifuge 10 min. at 13 000 RPM;
Remove the supernatant and dry the pellet by reversing the tubes (dry the cap of the EPPENDORF); and
Detach the pellet in 400 μL TE20:1 (20 mM TRIS buffer + 1 mM EDTA). If the restriction enzyme to be used does not have a high temperature of digestion (50° C. or more), incubate the tube at 65° C. for a few hours before adding the restriction enzyme.

Note: It is possible to use the same 1.5 mL EPPENDORF tube from the beginning to the end of the procedure.

Microsatellite $(TA)_n$ polymorphism analysis

The 88 subjects were subsequently genotyped for a known dinucleotide microsatellite $(TA)_n$ 5' to the ER gene (GDB # G00-162-541) that had 17 alleles and showed 82% heterozygosity in a previous report. PCR was carried out in an MJ PTC-100 thermocycler with hot-bonnet (MJ Research Inc, Watertown, Md.). Each 50 μL reaction contained 250 ng of genomic DNA, 40 nM of end-labeled with [gamma $^{32}$P] dATP forward primer 5' GACGCATGATATACTTCACC 3' (SEQ ID No: 3) and 200 nM of reverse primer 5' GCAGAATCAAATATCCAGATG 3' (SEQ ID No: 4) 200 μM of each dNTP, 3.5 mM $MgCl_2$, 15% glycerol and 2.5 U of ULTRATHERM DNA polymerase and buffer (Biocan Scientific Inc, Mississauga, Ont). Amplification conditions were: initial denaturation for 7 min. at 96° C. followed by 30 cycles of amplification with denaturation at 94° C. for 30 s, annealing at 50° C. for 45 s and polymerase extension at 72° C. for 60 s. A final extension at 72° C. for 2 min. was included. 5μL of the PCR reaction were then mixed in the same volume of loading buffer (Bromophenol blue) and 5–6μL of the mixture were deposited and the radiolabeled products were resolved on a 6% denaturing polyacrylamide gel electrophoresis, exposed overnight at room temperature and visualized by autoradiography.

Statistical analysis

ANOVA analyses were performed given the fact that the dependent variables were continuous (bone density measurements at different sites) and the independent variables were ordinal (genotypes at the VDR and ER genes). The significance level was set at alpha=0.05. A Chi square analysis was performed to study the level of linkage disequilibrium between the two different ER polymorphisms.

Results

PvuII RFLP

Typing of the ER receptor gene alleles using PCR followed by PvuII digestion of the PCR products was performed on the 88 samples of women between 60 and 70 years old. This RFLP has two alleles, namely p and P and each individual having two chromosomes 6 carries two copies of the ER gene and hence, two alleles of the RFLP. The various combinations of these two possible alleles generates three different genotypes at this locus: pp, pP and PP. Where "pp" designates homozygotes for the presence of the PvuII site, "PP" is for homozygotes for the absence of the PvuII site, and "pP" is for heterozygotes for the PvuII site with one allele with the presence of the site and the other with the absence of the site.

Figure 1B:
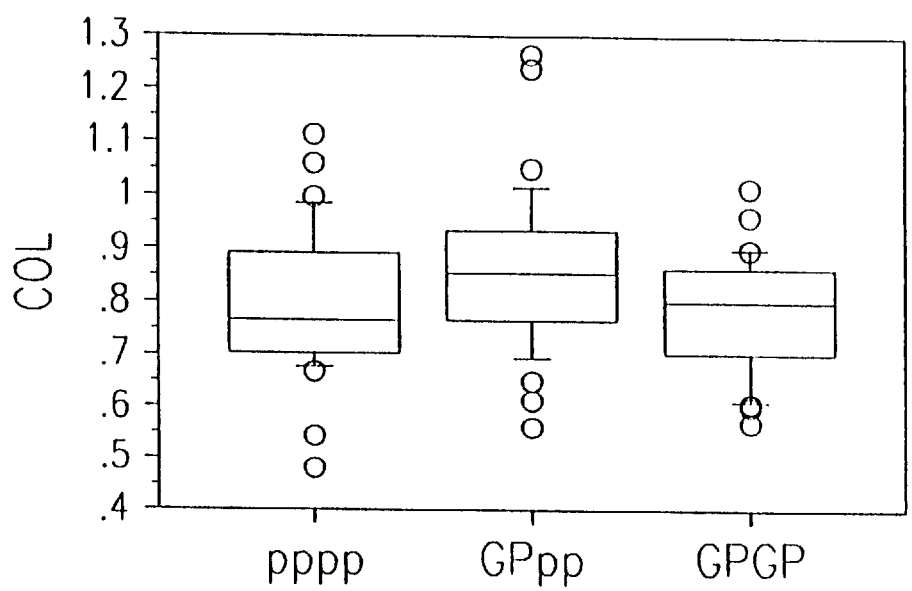
FIG. 1B is a box plot graph of the ER/PvuII RFLP genotyping results correlated with bone mineral density at the hip.

ER/PvuII RFLP genotyping results were correlated with bone mineral density as determined by DEXA at the L2–L4 vertebrae (FIG. 1A) as well as at the hip (FIG. 1B). ANOVA analysis showed that the ER genotype was a strong predictor of BMD at the L2–L4 level (p=0.0097) composed mainly of trabecular bone as well as at the hip (p=0.0387), which is composed principally of cortical bone. In fact, the ER genotype could divide women in two groups with a mean difference in BMD at L2–L4 of 0.12 g/cm3 (11%) and at the hip of 0.08 g/cm3 (10%). This represents a one standard deviation difference between the mean BMD at each site between the two groups of women as specified by the ER genotyping.

Unexpectedly, individuals homozygous for either of the ER alleles (pp or PP) had comparable mean BMD (no statistical difference, p>0.05) at both sites studied. However, their BMD was one standard deviation below those women heterozygous for the ER genes (pP). A one standard deviation difference in bone mineral density in elderly women is well known to be associated with an increased relative risk of bone fracture of about 2.4.

Hence, ER genotyping using the PvuII RFLP system allows to classify women in two groups (homozygotes vs. heterozygotes) that have a more than two-fold difference in the risk of bone fracture.

Microsatellite

In order to test for the hypothesis of a founder effect in the variation at the ER genotype observed in the population, all samples were retested with a ER gene microsatellite. This highly polymorphic genetic marker had a bimodal allele distribution (Table 2) and hence the alleles were grouped into two categories (E=alleles D to G; M=alleles H to P) to form a biallelic system generating three possible genotypes (EE, EM, MM). The microsatellite genotypes were highly correlated with the RFLP genotypes (Table 3) (p<0.0001) confirming a limited number of ER alleles present in the population. However, the linkage disequilibrium observed was not absolute (Table 2). When the microsatellite genotypes were correlated with BMD measurements, only a trend was observed (p=0.11), one of the between group comparisons was barely significant (EM vs. MM: p=0.05, mean difference in BMD=0.09 g/cm2) but in the same direction as the strong correlation observed with the PvuII RFLP.

TABLE 2

Allelic frequencies for ER -MS

| | Allele | | | | | | | | | | | |
|---|---|---|---|---|---|---|---|---|---|---|---|---|
| | D | E | F | G | H | I | J | K | L | M | N | O | P |
| Absolute | 10 | 45 | 10 | 1 | 3 | 3 | 6 | 8 | 13 | 17 | 11 | 7 | 4 |
| Relative (%) | 7 | 33 | 7 | 1 | 2 | 2 | 4 | 6 | 9 | 12 | 8 | 5 | 3 |

TABLE 3

Contingency table of PvuII RFLP vs ER -MS
Observed Frequencies for ER, ERms

| | EE | EM | MM | Totals |
|---|---|---|---|---|
| pp | 20 | 6 | 2 | 28 |
| pP | 3 | 25 | 4 | 32 |
| PP | 2 | 2 | 19 | 23 |
| Totals | 25 | 33 | 25 | 83 |

There is shown in Table 3 an example of the linkage disequilibrium between the alleles p and E, where the homozygotes EE are associated with the homozygotes pp.

Discussion

Previous studies have reported the effect of genetic variation of the VDR gene on BMD in women and the results appear contradictory. Whether these discrepancies are due to differences in the samples studied, or differences in methodological or data analysis approaches, or correspond to real differences between the populations studied has to be resolved. We did not find any effect of the VDR genotype on BMD of those women included in the present study but the effects of genetic variation of another important steroid receptor gene, namely the estrogen receptor (ER), were also analyzed.

In accordance with the present invention, it is demonstrated that genotyping at the ER gene allows one to predict whether women will be at increased risk of osteoporosis and bone fracture when they reach 60 years old. Because the ER genotype is genetically determined and remains the same throughout life, it is possible to genotype at the ER gene young women who have not yet reached their peak bone mass and concentrate preventive actions to increase BMD or diminish bone loss for those women which have a homozygous ER genotype as they will have, as a group, a BMD one S.D. below heterozygotes (i.e. more than twice the risk of osteoporosis) when they reach 60 years of age.

It is also important that the ER genotype was correlated with both BMD of trabecular bone and cortical bone which are two metabolically different types of bone. Furthermore, the intensity of the effect of the ER genotype was similar (i.e. one Standard Deviation) for each type of bone. ER genotyping thus may be a good marker of the homeostatic set point of general bone metabolism.

It is worth mentioning the unexpected relationship between the ER genotypes and BMD at the hip and vertebrae. The results reported by Morrisson et al. on the relationship of VDR genotypes with BMD showed a cumulative (or dosage) effect of one allele over the other i.e. that the BMD increased with the number of copies of a given allelic variant of the VDR gene (Morrisson NA et al., Nature, 1994, 367:284–297). The present analyses of the ER genotypes revealed an interaction (or inverted-"v" shaped) effect instead of a cumulative effect with the best predictor of a low BMD being the presence of identical (homozygous) alleles of the ER gene. This group of women (pp or PP) represented 60% of the (sample studied.

This simple genetic test of the ER genotype could also potentially be used to identify, prior to their menopause or later, which women would most benefit of estrogen replacement therapy or preventive pharmacotherapy (such as with biphosphonates). Further studies may also reveal that the clinical response to such therapies could be related to the ER genotype. Also, ER genotyping, as it is inexpensive, may be used to screen post-menopausal women to identify a subgroup which is at higher risk of low BMD and who could benefit from a more formal BMD measurement such as DEXA (which is too expensive to be offered as a screening procedure). Hence genotyping of the ER could become a fundamental parameter in prediction and management of low BMD as well as for the establishment of population-based osteoporosis prevention and intervention programs.

Also, typing of both the VDR and ER gene polymorphisms may enable a better prediction of BMD even if we did not find such a performance in the population studied. It is however likely that the association of ER genotyping with other analytical procedures (measurement of bone metabolites, other genotypes, etc.) may allow an even better discrimination between women of high and low risk for osteoporosis.

The biological mechanisms by which this strong effect of the ER genotype on trabecular and cortical BMD take place remains unknown. However, given the very peculiar correlation between the genotypes and the BMD measurements, it is tempting to speculate that the lower BMD in ER homozygotes vs ER heterozygotes may indicate that there is a difference in the physiological performance of heteroduplex estrogen receptors as compared to homoduplex estrogen receptors. One possible mechanism is, hence, that the mutation (or polymorphism) involved affects the dimerization domains of receptor monomers and influences the control of bone metabolism by the steroid hormone. This could be confirmed once the mutation involved in this ER effect on BMD after 60 years of age is identified; probably, the PvuII RFLP is closely associated with the effective ER gene mutation that has yet to be identified by sequencing.

Other mechanisms of action of ER gene polymorphism can also be postulated, including the effect of heterodimeric receptors on hormone or DNA binding or even on binding with other proteins involved in the availability or efficiency of ER receptors for the hormonal control of genes and cellular processes.

The present work demonstrating ER genotype effects on a disease clearly associated with estrogen metabolism opens the field of other estrogen-dependent diseases/conditions such as arteriosclerosis, endometriosis, breast cancer, ovarian cancer, and other estrogen-dependent cancers.

We have demonstrated for the first time that estrogen-dependent cellular processes can vary from one individual to the other according to the combination of estrogen receptor variants (or to the estrogen receptor genotype). Since there is only one estrogen receptor gene per haploid human genome (each cell contains two haploid genomes), the differences in biological efficacy of the estrogen hormone via the estrogen receptor genotype disclosed in the present application will also apply to other estrogen dependent diseases or conditions.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

or mutation which shows linkage disequilibrium with one of the alleles of the PvuII polymorphism located in the first intron of the estrogen receptor gene.

What is claimed is:

1. A method of determining predisposition to low or high bone density of a human patient, which comprises determining estrogen receptor polymorphism in linkage disequilibrium in a biological sample of said human patient, wherein heterozygosity is associated with high bone density and homozygosity is associated with low bone density, said estrogen receptor polymorphism being selected from the ground consisting of a PvuII polymorphic site located in the first intron of the estrogen receptor gene and a DNA variant or mutation which shows linkage disequilibrium with one of the alleles of the PvuII polymorphism located in the first intron of the estrogen receptor gene.

2. The method of claim 1, wherein detecting said estrogen receptor polymorphism comprises analysis of a restriction fragment length polymorphism using endonuclease digestion.

3. The method of claim 2, which further comprises a step prior to said estrogen receptor gene digestion, wherein at least a fragment of said estrogen receptor is amplified.

4. The method of claim 1, wherein said polymorphism of the estrogen receptor gene is detected using at least one oligonucleotide specific to the normal or variant estrogen receptor gene allele.

5. The method of claim 3, wherein said fragment of said estrogen receptor is amplified by polymerase chain reaction.

6. The method of claim 1, wherein low bone density is predisposition to osteoporosis and/or bone fracture of said patient during post-menopause.

7. The method of claim 1, wherein high bone density is indicative of resistance to osteoporosis and/or bone fracture of said patient during post-menopause.

8. The method of claim 1, wherein estrogen receptor genotyping is indicative of response to therapy and/or to preventive treatments against low bone mineral density and bone and vertebrae fractures.

9. A prognosis kit for determining predisposition to low or high bone mineral density of a human patient, which comprises at least a probe specific for estrogen receptor wherein said probe is capable of detecting an estrogen receptor polymorphism, said estrogen receptor polymorphism being selected from the group consisting of a PvuII polymorphic site located in the first intron of the estrogen receptor gene and a DNA variant or mutation which shows linkage disequilibrium with one of the alleles of the PvuII polymorphism located in the first intron of the estrogen receptor gene.

10. The method of claim 1, where said linkage disequilibrium is statistically significant by the Chi square test.

11. The method of claim 1, wherein said estrogen receptor polymorphism is the PvuII polymorphism.

12. The kit of claim 9, wherein said kit further comprises instructions for the diagnosis of a predisposition to low or high bone density.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGCCACCCTA TCTGTATCTT TTCC        24

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCTTTCTCTG CCACCCTGGC GTC        23

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GACGCATGAT ATACTTCACC        20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCAGAATCAA ATATCCAGAT G        21